United States Patent [19]

Bai et al.

[11] Patent Number: 4,495,792
[45] Date of Patent: Jan. 29, 1985

[54] METHOD FOR SIMULATING A SHOCK PULSE

[75] Inventors: Monty W. Bai, Scottsdale; Alfred B. Meyer, Mesa, both of Ariz.

[73] Assignee: Motorola, Inc., Schaumburg, Ill.

[21] Appl. No.: 490,694

[22] Filed: May 2, 1983

[51] Int. Cl.³ ............................................. G01N 3/30
[52] U.S. Cl. ...................................................... 73/12
[58] Field of Search ........................... 73/12, 432 SD

[56] References Cited

U.S. PATENT DOCUMENTS

| | | | |
|---|---|---|---|
| 2,763,148 | 9/1956 | Hoppmann | 73/12 |
| 3,100,983 | 8/1963 | De Vost | 73/12 |
| 3,106,834 | 10/1963 | Parstorfer | 73/12 |
| 3,194,052 | 7/1965 | Melzer | 73/12 |
| 3,209,580 | 10/1965 | Colby | 73/12 |
| 3,224,249 | 12/1965 | Ford et al. | 73/12 |
| 3,369,521 | 2/1968 | Meeder, Jr. | 73/12 X |
| 3,426,578 | 2/1969 | Bergs et al. | 73/12 |
| 3,597,969 | 8/1971 | Carchack | 73/12 X |
| 3,693,432 | 9/1972 | Stewart et al. | 73/12 X |
| 4,085,609 | 4/1978 | Kelly | 73/12 X |

FOREIGN PATENT DOCUMENTS

| | | | |
|---|---|---|---|
| 451948 | 3/1975 | U.S.S.R. | 73/12 |
| 509809 | 9/1976 | U.S.S.R. | 73/12 |
| 807101 | 2/1981 | U.S.S.R. | 73/12 |
| 922579 | 4/1982 | U.S.S.R. | 73/12 |

OTHER PUBLICATIONS

AVCO Shock Test Machine, Model SM-020, description 2 pp., 10-1963, Industrial Products Subdivision, AVCO.

Barry type 15575 Varipulse Shock Machine Advertisement, 2 pp., Bulletin 57-061, 6-1960, Barry Controls Inc.

Impac 1000 Shock Test Machine Advertisement, 2 pp., 12-1961, Monterey Research Laboratory, Inc.

Primary Examiner—Gerald Goldberg
Assistant Examiner—Tom Noland
Attorney, Agent, or Firm—Eugene A. Parsons

[57] ABSTRACT

A method for simulating a shock pulse on an encapsulated component wherein the encapsulated component is placed in a specimen container attached to an end of a pressure bar having a mass and a drop height chosen to simulate the shock pulse. The specimen container attached to the pressure bar is dropped on an anvil and the resulting shock pulse is monitored using strain gauges. Otherwise unencapsulated components may also be tested by this method if the component is surrounded by resilient material before testing.

7 Claims, 3 Drawing Figures

METHOD FOR SIMULATING A SHOCK PULSE

BACKGROUND OF THE INVENTION

The present invention pertains in general to shock pulse testing methods and in particular to methods for simulating shock pulse on an encapsulated component.

It is generally known that a pressure bar can be used as a dynamic loading device by slowly pushing down on a specimen to find its strength. However, it is generally believed that a specimen attached to a pressure bar cannot be used to accurately simulate a high acceleration load on a fuze or on its components by dropping the bar onto an anvil because of the presence of harmonics characteristic of a pressure bar having a certain length. As a consequence, relatively complicated gun shock simulators, such as the simulator shown in U.S. Pat. No. 3,693,432, have been constructed.

Because gun shock simulators rely upon recreating artillery conditions, projectile spin and other factors make it difficult or impossible to monitor transient failures in electronic components. This inability is particularly troublesome when a component is not destroyed but only malfunctions during flight. Furthermore, gun shock simulators are expensive and difficult to use.

Summary of the Invention

Accordingly it is an object of the present invention to provide a new and improved method of simulating a shock pulse on an encapsulated component.

Another object of the present invention is to provide a new and improved method for simulating a shock pulse on an unencapsulated structure.

Among the advantages of the present invention is the ability to easily and inexpensively test electronic components for use in projectiles. A further advantage of the present invention is that it allows monitoring of the component during application of the shock pulse in order to identify transient failures.

These and other objects and advantages of the present invention will become apparent to those skilled in the art upon consideration of the accompanying specification, claims and drawings.

In order to attain the above-mentioned and other objects and advantages the present invention involves a method for simulating a shock pulse on an encapsulated component. The method according to the present invention comprises the steps of providing a pressure bar, an anvil, an encapsulated component and a specimen container and choosing a mass and a drop height for a pressure bar suitable to stimulate a desired shock pulse. The method further comprises placing the encapsulated component in the specimen container and fixing the position of the pressure bar at the chosen height above the anvil so that an end of the pressure bar is directed toward the anvil. The specimen container is affixed to the end of the pressure bar and is directed toward the anvil. The pressure bar is released so that the specimen container strikes the anvil. Effects of the shock pulse resulting from the striking of the anvil by the pressure bar and by the specimen container are monitored.

DESCRIPTION OF THE PREFERRED EMBODIMENT

Figure 1:
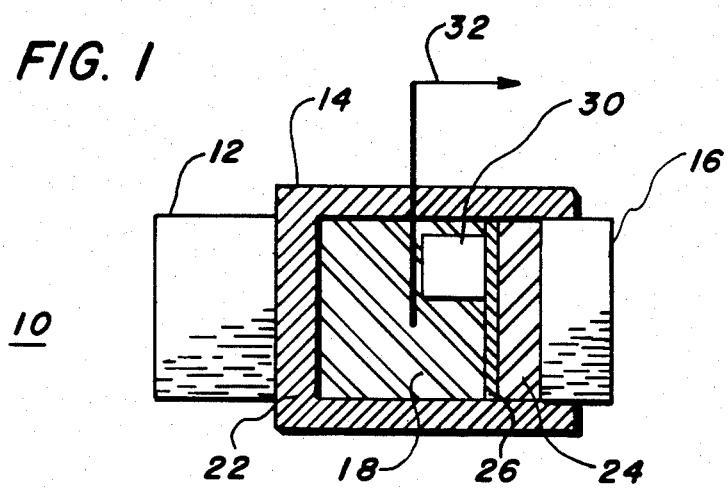
FIG. 1 is a view in vertical cross section through a specimen testable according to the method of the present invention.

In FIG. 1, a projectile component 10 has a first structural member 12, which may be described as a base member. Member 12 is attached to a container 14 which is in turn attached to a second structural member 16. Within cylindrical container 14 a first cylindrical encapsulant plug 18 separates a plate portion 26 from a closed end 22 of container 14. A second cylindrical plug of encapsulant 24 separates plate portion 26 from structural member 16. Plugs 18 and 24 surround an electronic component 30 which is affixed to plate 26. Component 10 experiences an acceleration $d^2Y_3/dt^2$ in direction 32 during application of a shock pulse.

Figure 2:
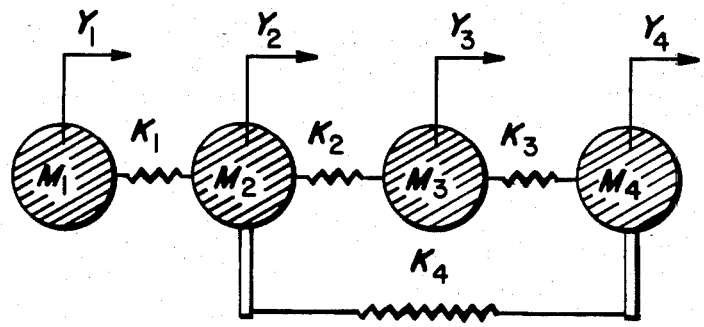
FIG. 2 shows a lumped mass-spring-damper model of the structure of FIG. 1.

FIG. 2 depicts a lumped mass-spring-damper model of the structure of FIG. 1. In FIG. 2, $Y_1$ = the linear displacement of element 12,
$Y_2$ = the linear displacement of element 14,
$Y_3$ = the linear displacement of plate 26 and attached element 30,
$Y_4$ = the linear displacement of element 16,
$m_1$ = the mass of element 12,
$m_2$ = the mass of element 14,
$m_3$ = the combined mass of elements 26 and 30,
$m_4$ = the mass of element 16,
$K_1$ = the spring constant for the interface between masses $m_1$ and $m_2$,
$K_2$ = the spring constant for the encapsulant interface between the masses $m_2$ and $m_3$,
$K_3$ = the spring constant for the encapsulant interface between masses $m_3$ and $m_4$, and
$K_4$ = the spring constant for the interface between masses $m_2$ and $m_4$.

In order to determine the proper excitation to be applied to the model as illustrated in FIG. 2, a mass-spring-damper model of an entire projectile is produced. For the projectile model, the equations of motion with forcing due to pressure loading are in matrix form, $$[M]\{d^2X_i/dt^2\} + [C]\{dX_i/dt\} + [K]\{X_i\} = \{P(t)\} \quad (1)$$

$$\{dX_i(0)/dt\} = \{X_i(0)\} = \{0\}, i=1,2,\ldots,n \quad (2)$$

where $d^2X_i/dt^2$, $dX_i/dt$ and $X_i$ are the linear acceleration, velocity and displacement of the ith mass, respectively. [M], [C] and [k] are the mass, damping and stiffness matrices, respectively. These differential equations may be solved by numerical integration based on the weighted average method.

The lumped mass-spring-damper model of the entire projectile yields a response acceleration time history. This acceleration time history, $d^2X_3/dt^2$, corresponds to the base input acceleration for the lumped mass-spring-damper model shown in FIG. 2. In terms of the relative coordinates in matrix form the governing equations of motion and initial conditions of the model in FIG. 2 are, $$[M]\{d^2Z_i/dt^2\} + [C]\{dZ_i/dt\} + [K]\{Z_i\} = \{-M\}\{d^2X_3/dt^2\} \quad (3)$$

$$\{dZ_i(0)/dt\} = \{Z_i(0)\} = \{0\}, i=1,2,\ldots,4 \quad (4)$$

where $d^2Z_i/dt^2$, $dZ_i/dt$ and $Z_i$ are the linear acceleration, velocity and displacement, respectively, relative to the base 12 to which an input shock/acceleration, $d^2X_3/dt^2$, is applied. Therefore, the absolute accelerations may be obtained by adding the base acceleration to the relative accelerations, $d^2Z_i/dt^2$, i.e., $$\{d^2Y_i/dt^2\} = \{d^2Z_i/dt^2\} + \{d^2X_3/dt^2\}. \tag{5}$$

Differential equations (3) and (5) may be solved by numerical integration using the Runge-Kutta method which is based on a fourth order integration. Where the duration of the base input acceleration, $d^2X_3/dt^2$, is many times longer than the period of an encapsulated component's natural frequency the encapsulant material does not isolate it from the base acceleration/setback. However, under the same conditions the encapsulant component is well isolated from the shock associated with the high frequency vibration of the projectile.

Figure 3:
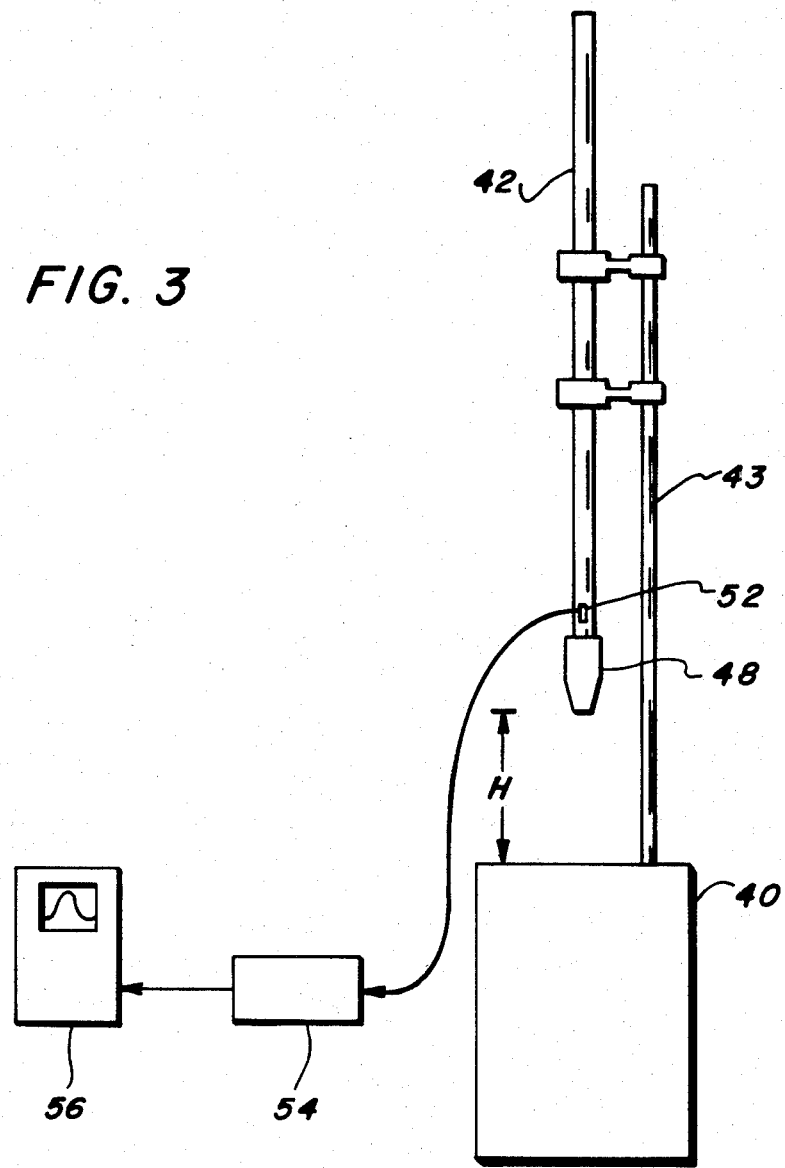
FIG. 3 depicts apparatus useful for performing the method according to the preferred embodiment of the present invention.

Therefore, the shock pulse applied to the structure of FIG. 1 during projectile setback may be simulated by a testing device which produces a haversine pulse load, a fact which is not appreciated by the prior art. testing device simulating the dynamic loading/setback on the electronic module is shown in FIG. 3. The loading device consists of a pressure bar 42, a specimen carrier cup 48, a guide rail 43, and an anvil 40. The device generates a haversine pulse load on component 10 placed within a carrier cup 48 at the impact end of the pressure bar. Because the compressional stiffness of the encapsulated component is far less than that of pressure bar 42, the motion of the pressure bar can be modeled with a single degree-of-freedom spring-mass system.

The governing equation of the linear motion during impact is $$md^2y/dt^2 + ky(t) = 0, \quad 0 \leq t \leq \pi/\omega \tag{6}$$

where m is the pressure bar mass and k is the module stiffness. The initial conditions are $y(0) = 0$ and $dy(0)/dt = \sqrt{2gh}$, where h is the drop height as shown in FIG. 3, and g is the acceleration of gravity (386.4 in/sec$^2$). The solution of Eq. (6) for the initial conditions is $$y(t) = \left(\frac{\sqrt{2gh}}{\omega_n}\right) \sin\omega_n t \tag{7}$$

where $\omega_n$ is the circular natural frequency of the system and is given as $\omega_n = \sqrt{k/m}$. The mass of the bar is selected so that the loading duration (haversine pulse) is equal to the setback duration (approximately 3.8 msec) to be simulated, i.e., $$m = \frac{D^2 k}{\pi^2} \tag{8}$$

where D is the desired loading duration. The maximum amplitude of acceleration may be obtained from Eq. (3) by differentiation, i.e., $$\left(\frac{d^2y}{dt^2}\right)_{max} = g\sqrt{\frac{2hk}{w}} \tag{9}$$

where w is the weight of the pressure bar. The required height for a given amplitude of the dynamic load may be obtained from Eq. (6) by using Newton's equation, $F = md^2y/dt^2$.

$$h = \frac{F^2}{2kw} \tag{10}$$

The dynamic loading time history is monitored by a set of strain gauges 52 located near the impact end. Note that the test simulates the resultant force time history from projectile setback rather than the setback acceleration. The output of gauges 52 is amplified by amplifier 54 and is displayed on cathode ray tube 56. Also note that failures may be detected during dynamic loading events.

All of the apparatus as shown in FIG. 3 is readily available to those skilled in the art. The mass of the specimen and cup being negligible, the mass of the bar determines the period of the applied pulse while a height H of container 48 above anvil 40 determines the amplitude of the pulse. The dynamic loading properties for a particular encapsulant may be determined mathematically or empirically (e.g. by static loading). The properties of the encapsulant, in particular its stiffness, may be inserted into the equations set forth above. Furthermore, the ability to monitor specimens tested according to the present invention permits adjustments of pressure bar length and drop height based upon the results of a few trial runs.

While the present invention has been described in terms of a preferred embodiment, further modifications and improvements will occur to those skilled in the art. For example, the method according to the present invention may be conveniently practiced on initially non-encapsulated components by surrounding such components with an encapsulated material, preferably a viscoelastic material, and then proceeding as if a normally encapsulated component were being tested. Surrounding a component in this way for all practical purposes eliminates the effect of pressure bar harmonics which would otherwise excite the component during testing.

We desire it to be understood therefore that this invention is not limited to the particular form shown and that we intend in the appended claims to cover all such equivalent variations which come within the scope of the invention as claimed.

We claim:

1. A method for simulating a shock pulse on an encapsulated component comprising the steps of:
    providing a pressure bar, an encapsulated component, a specimen container, and an anvil;
    choosing a pressure bar mass and drop height for simulating the shock pulse;
    placing said encapsulated component in said specimen container;
    fixing the position of said pressure bar at said height above said anvil so that an end of said pressure bar is directed toward said anvil;
    affixing said specimen container to said end of said pressure bar directed toward said anvil; and releasing said pressure bar so that said specimen container strikes said anvil.

2. The method according to claim 1 further comprising the step of monitoring effects of the shock pulse resulting from said pressure bar and said specimen container striking said anvil.

3. A method for simulating a shock pulse on an unencapsulated component comprising the steps of:
providing a pressure bar, an unencapsulated component, a resilient material, a specimen container, and an anvil;
choosing a pressure bar mass and drop height for simulating the shock pulse;
surrounding said component with said resilient material;
placing said unencapsulated component surrounded by said resilient material in said specimen container;
fixing the position of said pressure bar at said height above said anvil so that an end of said pressure bar is directed toward said anvil;
affixing said specimen container to said end of said pressure bar directed toward said anvil; and
releasing said pressure bar so that said specimen container strikes said anvil.

4. The method as recited in claim 3 wherein said resilient material is a viscoelastic material.

5. The method according to claim 3 further comprising the step of monitoring effects of the shock pulse resulting from said pressure bar and said specimen container striking said anvil.

6. The method as recited in claim 5 wherein said resilient material is a viscoelastic material.

7. A method of simulating a shock pulse on a component comprising the steps of:
providing a pressure bar having a mass, m;
fixing the component to one end of said pressure bar;
positioning said pressure bar vertically above a fixed anvil with the component at the lower end thereof; the component being positioned a distance, h, above the anvil;
choosing the mass, m, and distance, h, to simulate a shock pulse with a predetermined period and amplitude, respectively; and
dropping said pressure bar so that the component strikes the anvil.

* * * * *